(12) United States Patent
Du et al.

(10) Patent No.: US 7,550,278 B2
(45) Date of Patent: Jun. 23, 2009

(54) PROCESS FOR PRODUCING BIODIESEL FROM RENEWABLE OIL UNDER LIPASE CATALYSIS IN AN ORGANIC MEDIUM REACTION SYSTEM

(75) Inventors: Wei Du, Beijing (CN); Dehua Liu, Beijing (CN); Lilin Li, Beijing (CN)

(73) Assignee: Tsinghua University, Beijing (CN)

( * ) Notice: Subject to any disclaimer, the term of this patent is extended or adjusted under 35 U.S.C. 154(b) by 229 days.

(21) Appl. No.: 10/597,123

(22) PCT Filed: Nov. 29, 2004

(86) PCT No.: PCT/CN2004/001372

§ 371 (c)(1), (2), (4) Date: Dec. 1, 2006

(87) PCT Pub. No.: WO2005/075615

PCT Pub. Date: Aug. 18, 2005

(65) Prior Publication Data

US 2008/0038804 A1    Feb. 14, 2008

(30) Foreign Application Priority Data

Jan. 16, 2004   (CN)   .................... 2004 1 0000697

(51) Int. Cl.
C12P 7/62       (2006.01)
C11C 1/00       (2006.01)
C12P 7/64       (2006.01)
C12P 7/00       (2006.01)

(52) U.S. Cl. .................... 435/135; 435/41; 435/132; 435/134; 554/169

(58) Field of Classification Search .................... 435/41, 435/132, 134, 135; 554/169
See application file for complete search history.

(56) References Cited

U.S. PATENT DOCUMENTS 6,398,707 B1 *   6/2002   Wu et al. .................... 554/169

FOREIGN PATENT DOCUMENTS

| DE | 10217607 | | 10/2002 |
| DE | WO 03004591 | * | 1/2003 |
| JP | 11263750 | | 9/1999 |
| JP | 2002-23393 | * | 8/2002 |
| JP | 2002233393 | | 8/2002 |

OTHER PUBLICATIONS

Soumanou, M.M. et al., Improvement in Lipase-catalyzed synthesis f fatty acid methyl esters from sunflower oil, Jul. 16, 2003, Enzyme and Microbial Technology, vol. 33, pp. 97-103.*
JP 2002-233393, National Research Inst of Brewing, English translation, Aug. 20, 2002.*
WO 03004591, Siegfried et al., English translation, Jan. 16, 2003.*
Nie K., Wang F., Tan T. "Biodiesel Production by Immobilized Lipase";Modern Chemical Industry 23:9 (2003) pp. 35-38.
Shimada; Y.; Watanabe, Y.; Sugihara, A.; Tominaga, Y.; "Enzymatic alcoholysis for biodiesel fuel production and application of the reaction to oil processing"; Journal of Molecular Catalysis B: Enzymatic (2002) vol. 17, No. 32 pp. 133-142.
Nelson, L; Foglia, T. and Marmer, W.;"Lipase-Catalysed Production of Biodiesel"; Journal of the American Oil Chemists' Society, AOCS Press, Champaign, IL; vol. 73, No. 9, Sep. 1, 1996; pp. 1191-1195; XP000626753, ISSN: 003-021X.
Iso, M., Chen, B., Eguchi, M., Kudo, T. and Shrestha, S.; "Production of biodiesel fuel from triglycerides and alcohol using immobilized lipase"; Journal of Molecular Catalysis B: Enzymatic, Elsevier, Amsterdam, NL, vol. 16, No. 1 Nov. 20, 2001, pp. 53-58, XP002417337; ISSN: 1381-1177.

* cited by examiner

*Primary Examiner*—Porfirio Nazario Gonzalez
*Assistant Examiner*—Yate' K Cutliff
(74) *Attorney, Agent, or Firm*—Gottlieb, Rackman & Reisman, P.C.

(57) ABSTRACT

The present invention provides a new process for producing biodiesel from renewable oil under lipase catalysis in an organic medium reaction system. In this process, a short chain alcohol ROH is used as an acyl acceptor, a relatively hydrophilic organic solvent having no negative effect on the reactivity of lipase is used as the reaction medium, and a renewable oil raw material is catalyzed by a lipase to synthesize biodiesel through a transesterification reaction. In the process of the present invention, the renewable oil raw material can be almost completely converted into biodiesel and a byproduct glycerin, and the yield of the biodiesel is 94% or more. This new type organic medium reaction system promotes the solubility of the short chain alcohol in the renewable oil raw material, and dissolves part of the byproduct glycerin. Consequently, the reaction time is shortened, the productivity of biodiesel is increased and the reactivity and lifetime of the lipase is improved in the process of the present invention.

11 Claims, No Drawings

PROCESS FOR PRODUCING BIODIESEL FROM RENEWABLE OIL UNDER LIPASE CATALYSIS IN AN ORGANIC MEDIUM REACTION SYSTEM

TECHNICAL FIELD

The present invention relates to the field of bio-fuel synthesis, and more particularly, relates to a new process for producing biodiesel from renewable oil under lipase catalysis in an organic medium reaction system.

BACKGROUND

As a promising material of renewable oil industry, biodiesel is a long chain fatty acid ester produced from renewable oil through transesterification reaction. Biodiesel is a novel, pollutionless and recoverable energy source. The combustion performance of biodiesel is comparable with the conventional petroleum-based diesel, while after combustion, the content of harmful substances in the exhaust gas decreases approximately by 50% as compared with the conventional petroleum-based diesel. By far, wide attentions have been drawn to the studies and applications regarding biodiesel.

Currently, biodiesel is manufactured mainly through chemical methods. Particularly, vegetable oils and/or animal fats are used as a source of long chain fatty acids and a transesterification reaction between the long chain fatty acids and some short chain alcohols, such as methanol or ethanol, is carried out in the presence of an acid or base catalyst, and short chain ester of the fatty acids are obtained. However, some inevitable disadvantages exist in chemical methods as follows:

(1). Free fatty acid and water contained in the renewable oil raw material severely spoil the reaction;

(2). Emulsion is undesirably formed due to the poor solubility of alcohol in renewable oils, and the subsequent treatment steps are complicated;

(3). As required by the process, the amount of short chain alcohol used is much more than the reaction molar ratio, and the evaporation/reflux of the excess short chain alcohol leads to increased energy consumption.

In contrast, synthesizing biodiesel through a biological enzyme method has the following advantages: mild reaction conditions, non-toxic emissions, and enzyme-catalyzed reactions are not affected by the free fatty acid and small amount of water contained in the renewable oil raw materials. Therefore, bio-methods are consistent with the requirement of developing Green Chemistry, and thus have attracted more and more attention.

However, when compared with the chemical process, there exist some problems in the biological enzyme process. In an article entitled *Enzymatic alcoholysis for biodiesel fuel production and application of the reaction to oil processing* (Journal of Molecular Catalysis B: Enzymatic, 2002, 17:133-142) written by Shimada Yuji et al, it is reported that firstly, the poor solubility of short chain alcohols, such as methanol and ethanol, in the renewable oil raw material is unfavorable for the reaction; and secondly, the presence of the excess alcohol may lead to severe deactivation of the enzyme. Therefore, during the process of biodiesel production by the biological enzyme method, batch addition of short chain alcohol is generally adopted to moderate the poisonous effect imposed on the enzyme. However, this process is complicated in operation and needs long reaction time. Additionally, a short chain alcohol is used as an acyl acceptor, and byproduct glycerin is produced during the course of reaction, then the hydrophilic glycerin readily adheres to the inner pores and the outer surface of the immobilized enzyme forming a "shield" on the active sites of the enzyme, and severely affecting the reactivity of the enzyme. Furthermore, the yield of biodiesel synthesized by the enzyme process is relatively low compared with that by the conventional chemical process. To solve above-mentioned problems in a biological enzyme process, some scholars have tried to produce biodiesel in organic solvent reaction system. It is reported in an article entitled *Enzymatic alcoholysis for biodiesel fuel production and application of the reaction to oil processing* (Journal of Molecular Catalysis B: Enzymatic, 2002, 17:133-142) written by Shimada Yuji et al that, some relatively strong hydrophobic organic solvents, such as hexane, cyclohexane and petroleum ether can be used as reaction medium. These hydrophobic solvents can dissolve renewable oil very well, thus promoting the reaction to some extent. However, because these highly hydrophobic solvents can not dissolve lower carbon alcohol, such as methanol, as well as the byproduct glycerin effectively, the reactivity and lifetime of the enzyme, and the yield of biodiesel can not be improved notably.

SUMMARY OF THE INVENTION

Therefore, the object of the present invention is to provide a new process for producing biodiesel from renewable oil raw material under lipase catalysis in an organic medium reaction system. In this process, a short chain alcohol ROH is used as an acyl acceptor, a relatively hydrophilic organic solvent having no negative effect on the reactivity of lipase is used as the reaction medium, and a renewable oil raw material is catalyzed by a lipase to synthesize biodiesel through a transesterification reaction. The process of the present invention is characterized in that: a short chain alcohol and a renewable oil raw material having an alcohol/renewable oil molar ratio of 3:1 to 6:1, together with 20 to 200% by volume of an organic solvent based on the volume of the renewable oil, and 2 to 30% by weight of a lipase based on the weight of the renewable oil are added into an enzyme reactor and mixed evenly, and the mixture is heated to 20 to 60° C. to react for 4-24 hours to convert the renewable oil raw material into biodiesel and a byproduct glycerin.

BEST MODE OF THE INVENTION

In the process according to the present invention, said relatively hydrophilic organic solvent is preferably selected from the group consisting of tert-butanol and short chain fatty acid ester RCOOR', wherein R and R' are independently an alkyl group having 1-4 carbon atoms.

Said lipase is preferably a microorganism lipase, and is more preferably selected from the group consisting of Lipozyme® TL, Lipozyme® RM, Novozym® 435, and mixtures thereof.

Said renewable oil comprises biological renewable oils, and preferably comprises vegetable oil, animal oil and fat, waste edible oil and residues of refined oil.

Said vegetable oil comprises castor oil, rapeseed oil, soybean oil, peanut oil, corn oil, cottonseed oil, rice oil, algae oil and mixtures thereof.

Said animal oil and fat comprise fish oil, lard and mixture thereof.

In said short chain alcohol ROH, R is an alkyl group having 1 to 5 carbon atoms, and preferably said short chain alcohol comprises methanol, ethanol, propanol, butanol and pentanol.

Preferably, the reaction molar ratio of said short chain alcohol to said renewable oil is 3:1 to 5:1, and the amount of the organic solvent added is 50% to 100% by volume based on the volume of the renewable oil.

Said enzyme reactor may be a triangle flask with a plug, or other suitable enzyme reactors. Preferably, the heating step is carried out in an automatically thermostatic oscillating shaker or in various other bio-reactors suitable for enzyme catalyzed reaction. The preferred temperature for the reaction is 30 to 50° C.

The advantages of the process of the present invention comprise the improvement of the lipase reactivity, prolongation of the lifetime of the lipase, and remarkable increase in the yield of biodiesel. This new organic medium reaction system promotes the solubility of the short chain alcohol in the renewable oil raw material, and effectively decrease the negative influence imposed on the lipase reactivity by the short chain alcohol. In the organic medium reaction system, the desired short chain alcohol may be added in one step to shorten the reaction time notably, and the yield of biodiesel is increased to 94% or more. Furthermore, the relatively hydrophilic organic solvent dissolves part of the byproduct glycerin and thus the "shield" effect imposed on the immobilized lipase pores by glycerin is avoided, and the lipase reactivity and lifetime are improved.

The present invention is further illustrated by the following examples.

EXAMPLE 1

Into a triangle flask with a plug, methanol and rapeseed oil in a molar ratio of 4:1 (9.65 g rapeseed oil) together with 100% by volume of tert-butanol based on the volume of the rapeseed oil were added and mixed evenly, the flask was placed in an automatically thermostatic oscillating shaker, and the mixture was heated to 40° C., then 10% by weight of a immobilized lipase Novozym® 435 based on the weight of the rapeseed oil was added to start reaction, and the reaction was carried out for 6 hours. 9.64 g biodiesel was produced with an yield of about 100%.

EXAMPLE 2

Into a triangle flask with a plug, methanol and soybean oil in a molar ratio of 3:1 (9.65 g soybean oil) together with 20% by volume of tert-butanol based on the volume of the soybean oil were added and mixed evenly, the flask was placed in an automatically thermostatic oscillating shaker, and the mixture was heated to 20° C., then 2% by weight of immobilized lipase Novozym® 435 based on the weight of the soybean oil was added to start reaction, and the reaction was carried out for 24 hours. 9.17 g biodiesel was produced with an yield of 95%.

EXAMPLE 3

Into a triangle flask with a plug, ethanol and cottonseed oil in a molar ratio of 5:1 (9.65 g cottonseed oil) together with 200% by volume of methyl formate based on the volume of the cottonseed oil were added and mixed evenly, the flask was placed in an automatically thermostatic oscillating shaker, and the mixture was heated to 60° C., then 10% by weight of immobilized lipase Novozym® 435 based on the weight of the cottonseed oil was added to start reaction, and the reaction was carried out for 12 hours. 9.1 g biodiesel was produced with an yield of 94%.

EXAMPLE 4

Into a triangle flask with a plug, butanol and waste edible oil in a molar ratio of 3:1 (9.65 g waste edible oil) together with 80% by volume of tert-butanol based on the volume of the waste edible oil were added and mixed evenly, the flask was placed in an automatically thermostatic oscillating shaker, and the mixture was heated to 40° C., then 10% by weight of immobilized lipase Novozym® 435 based on the weight of the waste edible oil was added to start reaction, and the reaction was carried out for 7 hours. 9.65 g biodiesel was produced with an yield of 100%.

EXAMPLE 5

Into a triangle flask with a plug, methanol and soybean oil in a molar ratio of 3:1 (9.65 g soybean oil) together with 50% by volume of tert-butanol based on the volume of the soybean oil were added and mixed evenly, the flask was placed in an automatically thermostatic oscillating shaker, and the mixture was heated to 40° C., then 20% by weight of immobilized lipase Lipozyme® TL based on the weight of the soybean oil was added to start reaction, and the reaction was carried out for 10 hours. 9.1 g biodiesel was produced with an yield of 94%.

EXAMPLE 6

Into a triangle flask with a plug, pentanol and rapeseed oil in a molar ratio of 4:1 (9.65 g rapeseed oil) together with 100% by volume of butyl butyrate based on the volume of the rapeseed oil were added and mixed evenly, the flask was placed in an automatically thermostatic oscillating shaker, and the mixture was heated to 50° C., then 30% by weight of immobilized lipase Lipozyme® TL based on the weight of the rapeseed oil was added to start reaction, and the reaction was carried out for 8 hours. 9.17 g biodiesel was produced with an yield of 95%.

EXAMPLE 7

Into a triangle flask with a plug, ethanol and cottonseed oil in a molar ratio of 3:1 (9.65 g cottonseed oil) together with 80% by volume of tert-butanol based on the volume of the cottonseed oil were added and mixed evenly, the flask was placed in an automatically thermostatic oscillating shaker, and the mixture was heated to 40° C., then 20% by weight of immobilized lipase Lipozyme® RM based on the weight of the cottonseed oil was added to start reaction, and the reaction was carried out for 10 hours. 9.1 g biodiesel was produced with an yield of 94%.

EXAMPLE 8

The lipase remained after the reaction of example 1 was filtered and used in the next reaction batch, while other reaction conditions were kept as same as those in example 1, and the lipase was used repeatedly 10 times in the same way. During the $10^{th}$ reaction batch, 9.62 g biodiesel was produced with an yield of 99% after 6 hours of reaction.

According to the above-mentioned examples, when tert-butanol or a short chain fatty acid ester RCOOR' (wherein R and R' are independently an alkyl group having 1 to 4 carbon atoms) is used as an organic medium, and a short chain alcohol ROH (wherein R is an alkyl group having 1 to 5 carbon atoms) is used as an acyl acceptor, various renewable oil raw materials (castor oil, rapeseed oil, cottonseed oil, waste edible oil, soybean oil, fish oil, lard, residues of refined oil and algae oil, etc.) can be converted into biodiesel effectively under a suitable temperature condition upon the addition of 2 to 30% by weight based on the weight of the renewable oil of an immobilized lipase, such as Novozym® 435 (available from *Candida antarctica*), Lipozyme® RM (available from *Rhizomucor miehei*) and Lipozyme® TL (available from *Thermomyces lanuginosus*).

What is claimed is:

1. A process for producing biodiesel from renewable oil under lipase catalysis in an organic medium reaction system, wherein a short chain alcohol ROH, wherein R is an alkyl group having 1 to 5 carbon atoms, is used as an acyl acceptor, tert-butanol is used as a reaction medium, and a renewable oil raw material is catalyzed by a lipase to synthesize biodiesel through a transesterification reaction, characterized in that:

the short chain alcohol and the renewable oil raw material having an alcohol/renewable oil molar ratio of 3:1 to 6:1, together with 20-200% by volume of the tert-butanol based on the volume of the renewable oil, and 2-30% by weight of the lipase based on the weight of the renewable oil are added into an enzyme reactor and mixed evenly, the mixture is then heated to 20-60° C. to react for 4-24 hours to convert the renewable oil raw material into biodiesel and byproduct glycerin.

2. The process for producing biodiesel from renewable oil under lipase catalysis in an organic medium reaction system as claimed in claim 1, characterized in that:

said lipase is a microorganism lipase.

3. The process for producing biodiesel from renewable oil under lipase catalysis in an organic medium reaction system as claimed in claim 1, characterized in that:

said renewable oil is a biological renewable oil.

4. The process for producing biodiesel from renewable oil under lipase catalysis in an organic medium reaction system as claimed in claim 3, characterized in that:

said biological renewable oil comprises vegetable renewable oil, animal renewable oil, waste edible oil and residues of refined oil.

5. The process for producing biodiesel from renewable oil under lipase catalysis in an organic medium reaction system as claimed in claim 4, characterized in that:

said vegetable renewable oil comprises castor oil, rapeseed oil, soybean oil, peanut oil, corn oil, cottonseed oil, rice oil, algae oil and mixtures thereof.

6. The process for producing biodiesel from renewable oil under lipase catalysis in an organic medium reaction system as claimed in claim 4, characterized in that:

said animal renewable oil comprises fish oil, lard and mixture thereof.

7. The process for producing biodiesel from renewable oil under lipase catalysis in an organic medium reaction system as claimed in claim 1, characterized in that:

said short chain alcohol is selected from the group consisting of methanol, ethanol, propanol, butanol and pentanol.

8. The process for producing biodiesel from renewable oil under lipase catalysis in an organic medium reaction system as claimed in claim 1, characterized in that:

the molar ratio of said short chain alcohol to said renewable oil is 3:1 to 5:1.

9. The process for producing biodiesel from renewable oil under lipase catalysis in an organic medium reaction system as claimed in claim 1, characterized in that:

the amount of tert-butanol added as the organic medium is 50% to 100% by volume based on the volume of the renewable oil.

10. The process for producing biodiesel from renewable oil under lipase catalysis in an organic medium reaction system as claimed in claim 1, characterized in that:

the heating step is carried out in an automatically thermostatic oscillating shaker.

11. The process for producing biodiesel from renewable oil under lipase catalysis in an organic medium reaction system as claimed in claim 1, characterized in that:

the reaction temperature is in the range of 30° C. to 50° C.

* * * * *

UNITED STATES PATENT AND TRADEMARK OFFICE
Certificate

Patent No. 7,550,278 B2                                    Patented: June 23, 2009

On petition requesting issuance of a certificate for correction of inventorship pursuant to 35 U.S.C. 256, it has been found that the above identified patent, through error and without any deceptive intent, improperly sets forth the inventorship.
   Accordingly, it is hereby certified that the correct inventorship of this patent is: Wei Du, Beijing (CN); Dehua Liu, Beijing (CN); Lillin Li, Beijing (CN); Yuanyuan Xu, Beijing (CN); and Li Wang, Beijing (CN).

Signed and Sealed this Nineteenth Day of January 2010.

DANIEL M. SULLIVAN
*Supervisory Patent Examiner*
Art Unit 1621